United States Patent [19]

Steiger et al.

[11] Patent Number: 5,253,518

[45] Date of Patent: Oct. 19, 1993

[54] APPARATUSES AND METHODS FOR ADJUSTING A MATERIAL'S FLUID CONTENT AND EFFECTIVE STRESSES

[75] Inventors: Ronald P. Steiger, Houston; Peter K. Leung, Sugar Land, both of Tex.

[73] Assignee: Exxon Production Research Company, Houston, Tex.

[21] Appl. No.: 576,692

[22] Filed: Aug. 31, 1990

[51] Int. Cl.$^5$ ............................................. E21B 49/02
[52] U.S. Cl. ........................................ 73/153; 73/38; 73/151; 166/250
[58] Field of Search ................ 73/38, 594, 152, 153, 73/151; 166/250

[56] References Cited

U.S. PATENT DOCUMENTS

| | | | |
|---|---|---|---|
| 2,634,613 | 4/1953 | Napier | 73/38 |
| 2,703,977 | 3/1955 | Bailly | 73/38 |
| 2,705,418 | 4/1955 | Reichertz et al. | 73/38 |
| 2,737,804 | 3/1956 | Herzog et al. | 73/38 |
| 3,139,747 | 7/1964 | Ferrell et al. | 73/38 |
| 3,199,341 | 8/1965 | Heuer, Jr. et al. | 73/820 |
| 3,216,242 | 11/1965 | Eyrich | 73/38 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,610,032 | 10/1971 | Di Crispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,820,385 | 6/1974 | Cordoba | 73/84 |
| 3,881,345 | 5/1975 | Souder | 73/94 |
| 3,975,950 | 8/1976 | Erdei | 73/94 |
| 4,359,901 | 11/1982 | Bates et al. | 73/153 |
| 4,380,930 | 4/1983 | Podhrasky et al. | 73/594 |

(List continued on next page.)

FOREIGN PATENT DOCUMENTS

| | | | |
|---|---|---|---|
| 0252707 | 11/1968 | U.S.S.R. | 73/38 |
| 0794434 | 7/1981 | U.S.S.R. | 73/38 |

OTHER PUBLICATIONS

"Lateral-deformation Gage for Rock-mechanics Testing," by Karl W. Schuler, 1978.

"Drilling Fluids," Exxon Production Research Company, 1989.

"The Mechanics of Soils," Atkinson et al. 1978, pp. 118–144, 184–209, 292–343.

"Soil Mechanics," Lambe et al., 1969, Chapter 20, pp. 295–303.

"Quantitative Determination Of The Mechanical Properties Of Shales," Steiger and Leung, SPE Conference, Oct. 2–5, 1988.

"Predictions Of Wellbore Stability In Shale Formations At Great Depth," Steiger and Leung, SPE Symposium 1989.

"Acoustical Properties Of Clay Bearing Rocks," C. A. Tosaya, 1982.

Primary Examiner—Hezron E. Williams
Assistant Examiner—George Dombroske
Attorney, Agent, or Firm—Guy McClung

[57] ABSTRACT

Methods are disclosed for multi-stage tests of material samples, including but not limited to rock and shale samples, the methods, in one aspect, including the steps of placing a load on the sample, while under a constant confining pressure the sample mounted in a triaxial test apparatus; measuring and recording sample pore pressure continuously during the test; removing the load on the sample; changing confining pressure on the sample; permitting the sample's pore pressure to equilibrate at a new pore pressure with the new confining pressure; permitting the sample to drain fluid to an equilibrium value and placing a new load on the sample measuring and recording resulting pressure and load. In one embodiment these steps are repeated a plurality of times and a plurality of pore pressure, confining pressure, and load readings are obtained.

8 Claims, 11 Drawing Sheets

U.S. PATENT DOCUMENTS

| | | | |
|---|---|---|---|
| 4,430,890 | 2/1984 | Hains | 73/147 |
| 4,486,714 | 12/1984 | Davis et al. | 73/153 |
| 4,487,056 | 12/1994 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,566,311 | 1/1986 | Barnaby | 73/38 |
| 4,579,003 | 4/1986 | Riley | 73/784 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,625,544 | 12/1986 | Hi-Hwa Yuan et al. | 73/38 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,879,654 | 11/1989 | Bruce | 364/422 |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny | 73/865.6 |
| 5,025,668 | 6/1991 | Sarda et al. | 73/38 |
| 5,025,669 | 6/1991 | Sarda et al. | 73/798 |
| 5,065,421 | 11/1991 | Morineau et al. | 73/38 |
| 5,069,065 | 12/1991 | Sprunt et al. | 73/153 |

APPARATUSES AND METHODS FOR ADJUSTING A MATERIAL'S FLUID CONTENT AND EFFECTIVE STRESSES

BACKGROUND OF THE INVENTION

2. Field of the Invention

This invention is related to apparatuses and methods for adjusting a material's fluid content and effective stresses and, in one embodiment tests of geologic materials (e.g. soils, sands, clays, rocks, coal, etc.) and, in one aspect, to triaxial test apparatuses and methods for low permeability rock, e.g. shales, to determine various properties of the rock such as mechanical strength properties, stress history, compression (compaction), history, compressibility properties, effective stresses, and pore pressure. In certain embodiments this invention is directed to triaxial test apparatuses and methods for multi-stage tests of low permeability rocks in which a sample is stressed almost to failure at one water content or in which a sample is consolidated; some sample fluid is then expelled from the sample; and the test is then repeated at several water contents and then at a final water content is loaded to failure.

2. Description of the Related Art

Wellbore stability has been frequently identified as one of the major sources of trouble costs for drilling in shale. In order to minimize wellbore stability related trouble costs, testing programs have been developed to build data bases and generalize the mechanical properties of different shales. Very high quality and useful results have been obtained. However, such test programs are very tedious and require many tests (e.g. 15-20) to quantify the properties for one shale type.

FIG. 1 illustrates a conventional triaxial test apparatus for rock testing. The test is performed inside an enclosed hydraulic cell and a confining fluid pumped into the cell provides a confining pressure on a rock sample specimen to be tested. The rock sample is placed on the bottom end cap for support. During the test, hydraulic pressure is applied around the sample to generate an isostatic confining stress and then an axial load (usually via a load piston) is applied to the top end cap to generate a deviatoric (shear) stress. The prior art does not teach monitoring water content during a triaxial test nor does it teach controlling and adjusting water content of low permeability materials, such as shales. The prior art does not teach a multi-stage test wherein a low permeability rock sample is stressed to a point near its shear failure, without reaching shear failure, then withdrawing some sample fluid to increase the rock's pore pressure and to then again stress the rock, all in one test.

Applicants are unaware of any prior art disclosing triaxial test apparatuses and methods for multi-stage tests of low permeability rock, such as shales, which permit step-wise reduction and/or increase of sample water content. Applicants are also unaware of any prior art disclosing test apparatuses and methods that can accurately determine the strength—mean effective stress relationship of a low permeability material within one test.

There has long been a need for triaxial test apparatus and methods for low permeability rock for a multi-stage test. There has long been a need for such apparatuses and methods in which a single test of a relatively small amount of a core sample can yield a variety of properties. There has long been a need for triaxial test apparatuses and methods which could effectively and accurately measure different pore pressures in one sample of low permeability rock in one test.

SUMMARY OF THE PRESENT INVENTION

Our invention includes a new design of triaxial test apparatus which includes end caps and test procedures to measure various properties of low permeability rocks.

In one embodiment of a triaxial test apparatus according to the present invention, a rock sample mounting apparatus is provided which has a bottom end cap and a top end cap, each with a flat planar face for mounting below (bottom end cap) or above (top end cap) the flat face of the sample. A pore pressure channel extends from the top surface of the bottom end cap to a pore pressure port or chamber in the bottom end cap. It is preferred that the top end cap also has a pressure transducer in a pore pressure chamber in communication with a pore pressure channel and with related wiring. Sample fluid expelled from the rock sample during testing (e.g. water or some other fluid) flows into the pore pressure channel of the bottom end cap. One or more impermeable flexible jackets covering the side wall of the sample and extending slightly over the end cap to which it is secured prevents sample fluid from exiting from the top-end-cap-top-face-of-the-rock-sample interface. To promote fluid movement to the pore pressure channel, a screen or screens partially or totally enclose the sample and are applied before applying the flexible jacket(s). Sample fluid expelled into the pore pressure channel contacts a pore pressure fluid (preferably a fluid not miscible with the sample fluid) and compresses it somewhat. That compression causes a pressure change which is sensed by a pore pressure transducer in the pore pressure port and it is conveyed in analog form (change in voltage) via wiring from the pore pressure transducer to a monitor system (e.g. a computer which can also record data). Deformations in the sample due to the load on it are measured using strain indicators, preferably linear variable differential transformers (LVDT) for indicating vertical axial deformation and cantilevered strain gauges for indicating radial deformation. It is preferred that the pore pressure channel and pore pressure port (and the interior of a microaccumulator and lines to it) are small to minimize the effects of fluid compressibility.

By utilizing a high pressure fluid generator or microaccumulator in communication with the pore pressure port, fluid is withdrawn from a sample during testing by withdrawing pore pressure fluid from the pore pressure port during testing. Thus, the fluid content of the sample can be adjusted and controlled during a test, thereby varying and controlling a sample's mean effective stress during testing. The end caps are, preferably, made from high strength material, e.g. hardened steel or titanium.

With triaxial test apparatuses and methods according to this invention, a variety of mechanical tests on low permeability geologic materials, including but not limited to shales, are possible; e.g., multistage strength tests, compression tests, consolidation tests, pore volume compressibility tests, tests conducted isostatically or under a $K_o$ condition. A $K_o$ test allows no radial (transverse) displacement during the test.

A compression test according to the present invention starts with obtaining a well preserved and undisturbed rock sample cored from a wellbore. Then, a constant isostatic confining pressure, p, is applied on the rock sample in a triaxial cell. The sample's pore pressure is allowed to reach a predetermined value (e.g. 2000 p.s.i.). Pore pressure, u, is measured by the pore pressure sensor and the mean effective (confining) stress, p', defined as (p-u) is determined. Then a valve which is located on the stiff drainage line between the pore pressure port and the high pressure fluid generator or microaccumulator is opened to allow fluid to move out of the sample. The confining pressure and the measured pore pressure of the sample are maintained at a constant value until the fluid stops moving out from the sample. Then, additional confining pressure is added to the sample. The test is performed in multi-stages at different mean effective stresses. In each stage of the test, a small amount of water is withdrawn from the sample by adjusting a high pressure generator or accumulator. By letting small increments of water drain out from the sample, the water content of the sample decreases in steps. At the same time the pore pressure decreases gradually and the mean effective stress increases stepwise, accordingly. The next stage of the test does not start until a constant pore pressure is measured. By calculating the water content and mean effective stress for the end of each test stage, the water content and mean effective stress relationship for the sample is accurately defined within one test. The compression test also allows accurate determination of the sample's stress history, compression (compaction) history, and compressibility properties.

A stepwise strength that according to the present invention starts with obtaining a well preserved and undisturbed rock sample cored from a wellbore. Then a constant isostatic confining pressure, p, is applied on the rock sample in a triaxial cell. The sample pore pressure is allowed to reach to a predetermined value (e.g., 2000 p.s.i.) Then a valve which is located on the stiff drainage line between the pore pressure port and the high pressure fluid generator or microaccumulator is opened to allow fluid to move out of the sample. The pore pressure of the sample is maintained at a constant value until fluid stops moving out of the sample. After the sample reaches equilibrium with the confining pressure and the preset pore pressure, the valve is closed and the sample is loaded triaxially until it reaches a condition near shear failure. During the loading period, water is not allowed to move out of the sample. After the sample reaches an "almost failure" condition, the load is taken off from the sample and a higher confining pressure is applied to the sample. The valve is opened to allow fluid from the sample to move out. The test is performed in multistage of: increasing confining pressure, draining sample under a constant confining pressure and pore pressures, and loading to almost failure. This test provides a close approximation to failure envelope of a low permeability rock, such as shale, in one test. The prior art requires many tests to obtain such information.

It is, therefore, an object of the present invention to provide new, useful, unique, efficient and nonobvious triaxial test apparatuses and methods for measuring various properties of rocks, including low permeability rocks.

Another object of the present invention is the provision of devices and methods for adjusting pore pressure and water content of a sample.

Yet another object of the present invention is the provision of a multi-stage test which in one test provides mean effective stress data for a variety of different sample water contents.

A further object of the present invention is the provision of triaxial test methods and apparatuses with which the relationship between water content and mean effective stress can be determined in a single multi-stage test.

An additional object of the present invention is the provision of such methods and apparatuses in which only a very small amount of fluid is expelled from or injected into a sample during a test and then only a small amount of fluid is withdrawn from or injected into the sample to achieve a new fluid content.

Another object of the present invention is the provision of devices and methods for determining the stress history, compression (compaction) history and compressibility properties of low permeability rocks, such as shales, and generalizing the mechanical behavior of those rocks under the framework of critical state mechanics.

Appended hereto and included fully herein for all purposes are copies of the following applications filed on even date herewith and co-owned with this application:

"Methods and Apparatuses For Measurement Of The Strengths, Pore Pressures, And Mechanical Properties Of Low Permeability Geologic Materials," naming Mr. Ronald P. Steiger as inventor.

"Methods For Determining In Situ Shale Strengths, Elastic Properties, Pore Pressures, Formation Stresses And Drilling Fluid Parameters," naming Messrs. Ronald P. Steiger and Peter K. Leung as co-inventors.

"Apparatuses and Methods For Measuring Ultrasonic Velocities In Materials," naming Messrs. Ronald P. Steiger and Peter K. Leung as co-inventors.

"Microaccumulator For Measurement Of Fluid Volume Changes Under Pressure" naming Messrs. Ronald P. Steiger, Peter K. Leung and Rudolf J. Stankovich as inventors.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention

DESCRIPTION OF EMBODIMENTS PREFERRED AT THE TIME OF FILING FOR THIS PATENT

Figure 1:
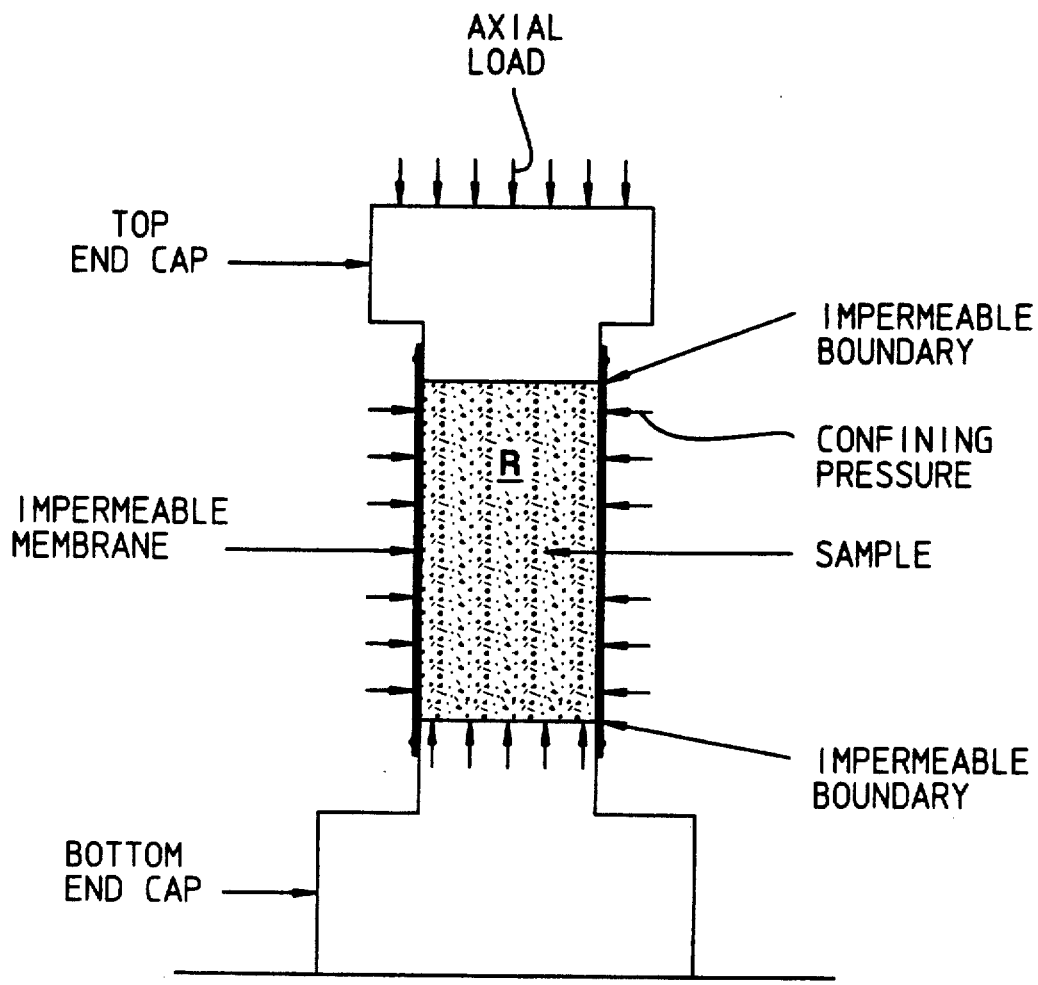
FIG. 1 is a schematic view of a prior art triaxial test apparatus.

Referring now to FIG. 1 a typical prior art triaxial test set-up is shown schematically. Mounting apparatus for a rock sample R includes a top end cap and a bottom end cap. An impermeable membrane (e.g. a plastic or rubber jacket or jackets) is placed over the sample R extend onto each end cap to which it is secured, e.g. by a wire rope creating impermeable boundaries at each end of the sample R. Appropriate strain indicators are applied to the sample to indicate the extent of deformation of the sample during testing. Cantilevered strain gauges and LVDT's (linear variable differential transformers) are used. The bottom end cap rests on a load cell (not shown) which indicates the amount of axial load applied to the sample R by a load piston (not shown). A confining fluid pumped into a sealed housing (not shown) into which the mounted sample R is placed provides a desired confining pressure on the sample. This pressure is measured by a transducer in the housing.

Figure 2:
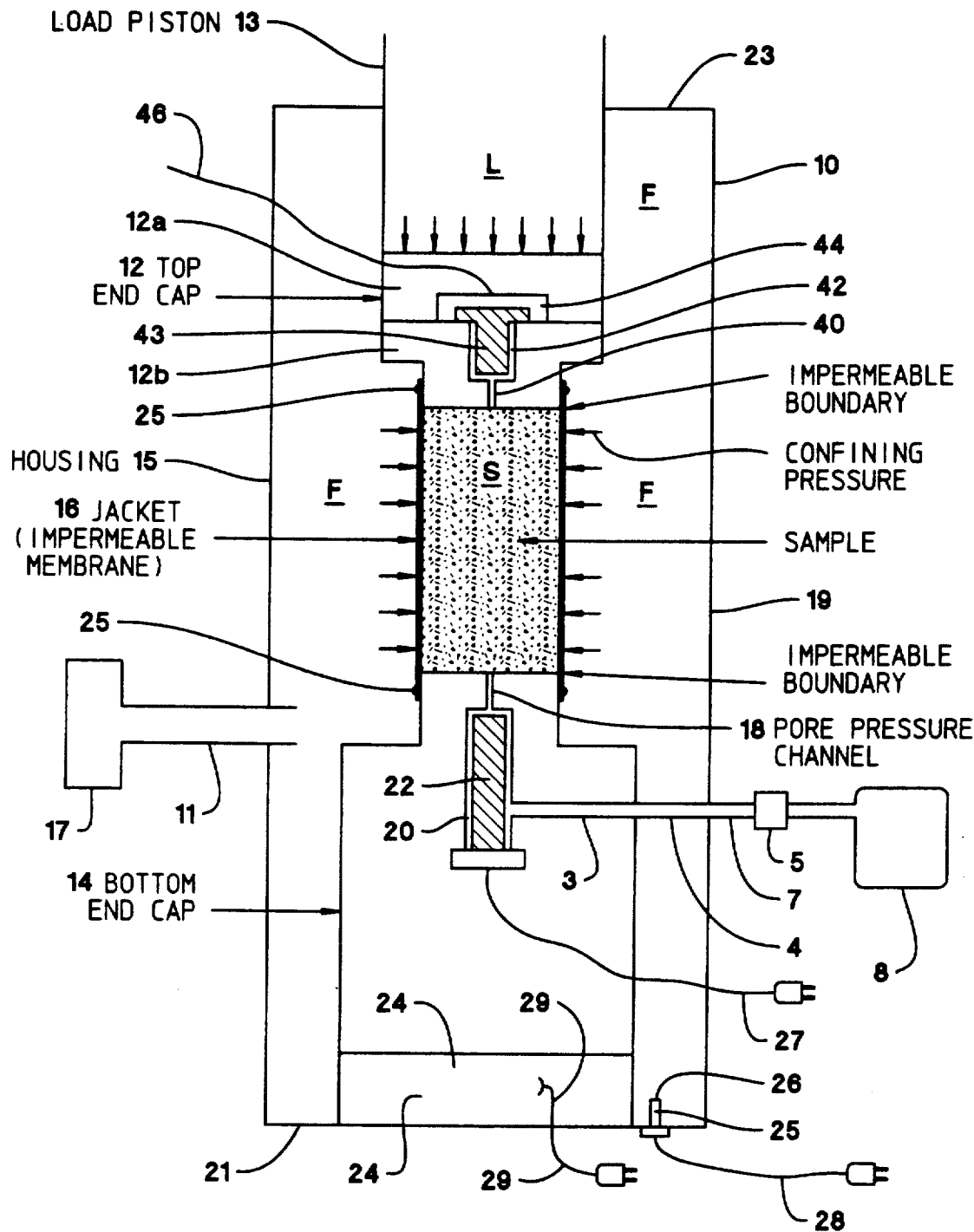
FIG. 2 is a schematic view of a triaxial test apparatus according to the present invention.

As shown schematically in FIG. 2, a triaxial test apparatus 10 according to the present invention has a housing 15 preferably made from titanium or high strength steel with a side wall 19, (preferably generally cylindrical) a bottom plate 21, and a top plate 23. The apparatus 10 has a top end cap 12 and a bottom end cap 14 that rests on a load cell 24 on which rests the bottom plate 21. A sample S, placed between the end caps, is sheathed with an impermeable jacket (or jackets) 16. A load piston 13 contacts the top end cap 12 and a portion of the piston extends sealingly through the top plate 23 of the housing 15. The load piston applies a load L to the sample S through the top end cap 12. A confining fluid pumping system 17 pumps and hydraulic fluid F into the housing 15 through a fluid line 11. As noted, additional jackets may be used. The end caps are made from high strength materials (e.g. titanium or hardened steel) and the boundaries between the end caps and the jacketed sample are impermeable. The jacket extends slightly beyond the sample on the end caps and wire ropes 25 secure the ends of the jacket about the end caps.

The end caps have flat, polished smooth surfaces for contacting the sample with diameters closely matched to that of the sample; i.e. it is preferred that they be within 0.005 inches of each other. Also, it is preferred that samples' ends' flatness be within about 0.001 inch per inch of diameter. This minimizes void space between end cap and sample; provides uniform loading of the sample; and minimizes unwanted end effects.

The bottom end cap 14 has a pore pressure channel 18 which communicates with a fluid port or chamber 20. A pore pressure transducer 22 is disposed in the fluid chamber 20. A non-wetting inert fluid immiscible in water or pore fluid (e.g. mercury) is placed in the pore pressure channel 18 and in the fluid chamber 20. Preferably, the pore pressure channel 18 and the fluid chamber 20 are vacuum evacuated prior to the introduction of mercury so that no air is trapped therein which could adversely affect test results. The pore pressure transducer 22 is an accurate miniature strain-gauge type pressure transducer interfaced via wiring 27 with a digital data acquisition system monitor/control (e.g. computer). A high pressure generator or microaccumulator 8 is in fluid communication with the pore pressure chamber 20 via a stiff conduit 7, a channel 3, and a stiff conduit 4. A valve 5 controls flow in the conduit 7. The top end cap 12 is comprised of two portions bolted together, 12a and 12b. In a pore pressure port 42 of a pore pressure channel 40 is disposed a pore pressure transducer with wiring 46, which partially extends in a recess 44 of the top portion 12a of the end cap. This transducer operates like the transducer 22.

The hydraulic fluid F surrounding the sample S provides a desired confining pressure for the sample S. A confining pressure transducer 25 mounted in a hole 26 in the plate 21 has wiring 28 leading to the computer. The load cell 24 has wiring 29 extending therefrom for interfacing with the computer. The load cell indicates the amount of axial load applied by the piston 13, through the top end cap, to the sample. Via a line 7 a microaccumulator or high pressure generator 8 (like item 320, FIG. 3 or like item 184, FIG. 4) is in communication with the pore pressure chamber 20.

Figure 3:
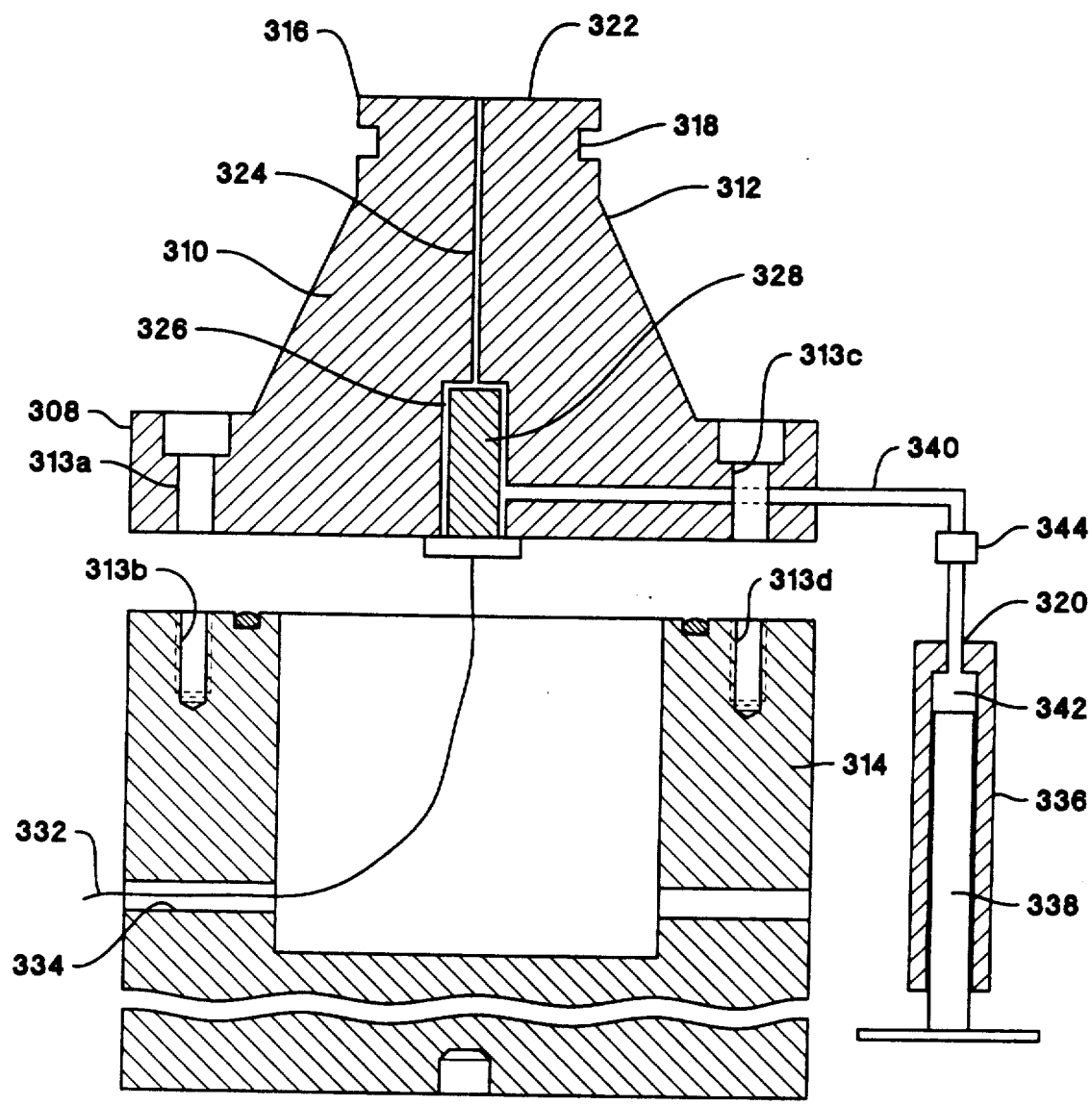
FIG. 3 is a side cross-sectional view of test devices including a triaxial test end cap and associated apparatus according to the present invention.

A test apparatus 308 according to the present invention is shown in FIG. 3 in cross-section with an end cap 310 and a high pressure generator 320 in communication therewith. The end cap 310 has a top portion 312 and a bottom portion 314 which are bolted together by bolts (not shown) extending through holes 313a, 313b, 313c, and 313d. An apex 316 of the top portion 312 has a groove 318 for receiving a portion of an impermeable flexible jacket or jackets (not shown) for enclosing the side of a rock sample.

A face 322 of the apex 316 is substantially flat for facing up against a flat surface of a rock sample; and it is preferred that the flatness of the face 322 vary only about 0.001 inch per inch of dimensional extent.

From the face 322 extends a pore pressure channel 324 in the end cap 310 which communicates with a pore pressure port 326 in the end cap 310. A pore pressure transducer 328 in the pore pressure port 326 senses changes in the pressure of a pore pressure fluid that fills the pore pressure port and the pore pressure channel. Sensed changes are conveyed via wiring 332 to a recorder or monitor (e.g. a digital data acquisition system or computer, not shown). The wiring 332 exits from the bottom portion 314 of the end cap 310 via a hole 334.

Sample fluid expelled from a rock sample mounted above the end cap 310 will move into the pore pressure channel 324 compressing a pore pressure fluid in the pore pressure channel 324 and in the pore pressure port 326. Preferably this pore pressure fluid is not miscible with the sample fluid; does not react with the sample or the sample fluid; is inert; and does not wet the sample. For example, of the sample fluid is water mercury is a preferred pore pressure fluid.

The high pressure generator 320 has a hollow body 336, preferably made from high strength material such as hardened steel or titanium, in which is movably, adjustably and sealingly mounted a piston 338. Pore pressure fluid fills a line 340 in communication with the pore pressure port 326 and an interior space 342 of the hollow body 336. A valve 344 controls flow in line 340. By moving the piston 338 outwardly, thereby increasing the volume of the interior space 342 that can receive pore pressure fluid, more sample fluid can be expelled from a rock sample mounted to the end cap 310. This makes it possible to remove sample fluid from a rock sample during a test to change the sample's water content and to thereby change the sample's mean effective stress.

It is preferred that the pore pressure channel and pore pressure port be very small in volume to minimize the effect of fluid compressibility on volume changes and on pore pressure responses.

Figure 4:
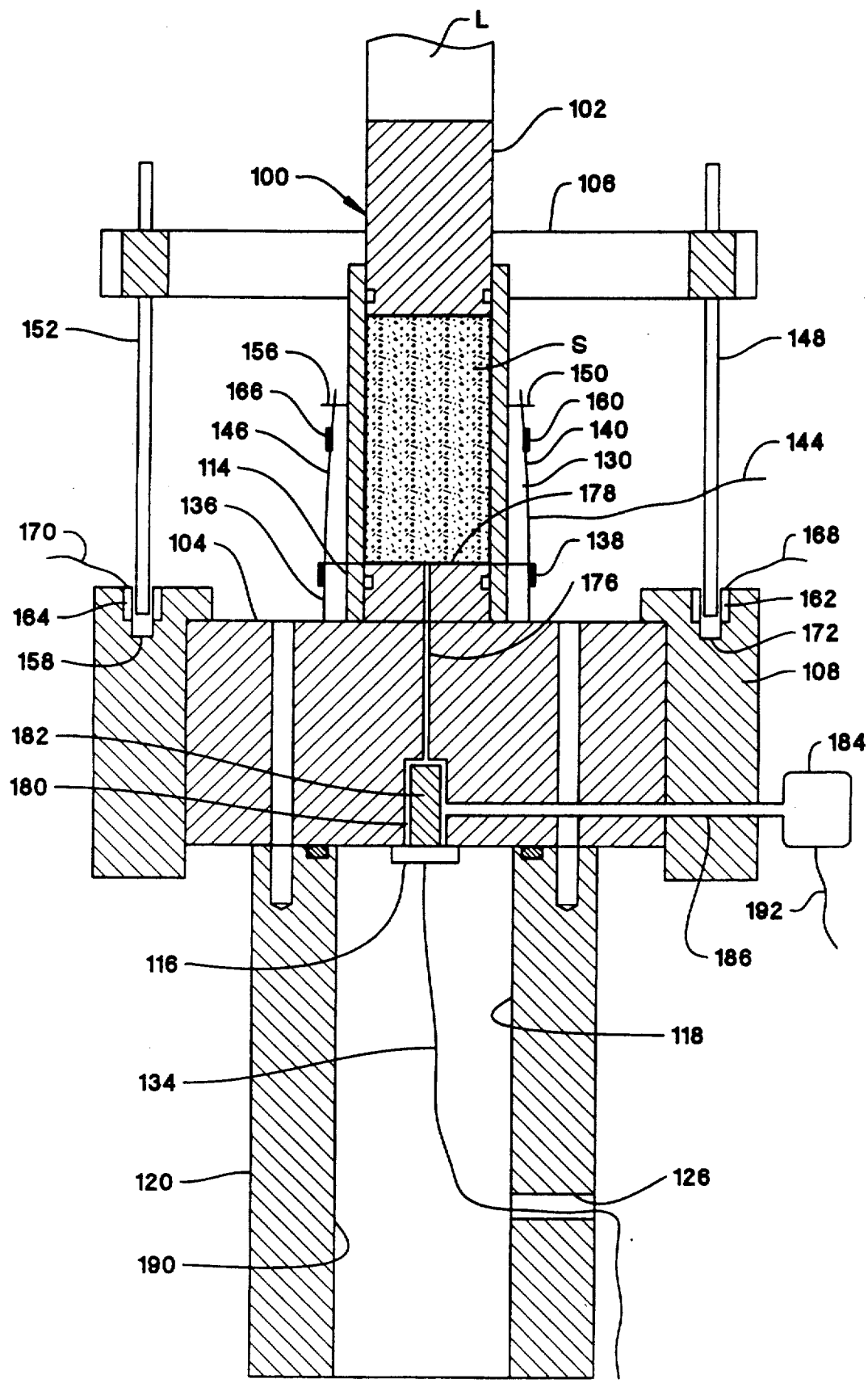
FIG. 4 is a side cross-sectional view of triaxial test apparatus according to the present invention.

FIG. 4 illustrates, partially schematically, a test apparatus 100 according to the present invention which has a top end cap 102 and a bottom end cap 104 mounted to a rock sample specimen S to be tested in a triaxial test cell (not shown). A holder 106 is secured to the top end cap 102 by set screws (not shown) and a collar 108 is secured to the bottom end cap 104. The bottom end cap 104 is secured to a bottom base 120 which is disposed on a load cell 128 for indicating the level of axial load on the sample. The base 120 can be placed on a load cell (not shown).

Cantilevered strain gauges 130 and 136 (more may be used, e.g. four or more spaced around the sample) are mounted to a mounting ring 138 which is secured about the sample S. Beams 140 and 146 extend upwardly from the ring 138 and pins 150 and 156 contact an impermeable flexible jacket 142 (or jackets) that surround the side wall of the sample S. Gauges 160 and 166 on the beams 140 and 146 sense radial deformation of the sample S during compressive loading by a load piston L. Via wiring 144 sensed changes are conveyed to a monitoring system (e.g. a computer).

To sense changes in axial (vertical) deformation of the sample, it is preferred although not necessary, that linear variable differential transformers LVDT's) be used because of their accuracy and sensitivity. The holder 106 is mounted to the top end cap 102. Secured to the holder 106 are LVDT rods 148 and 152 which extend into recesses 172 and 158 in the collar 108. The rods 148 and 152 are movable within, respectively, coils 162 and 164 disposed in the collar 108. Movement of the rods due to axial deformation of the sample S changes the voltage of the coil's and this change is conveyed to a monitoring system via wiring 168 and 170.

A pore pressure channel 176 extends from a top face 178 of the bottom end cap 104 and into a pore pressure port 180 in which is disposed a pore pressure transducer 182 for sensing changes in a pore pressure fluid in the port 180 due to sample fluid being expelled from the sample S during testing or due to pressure changes caused by a microaccumulator 184 which is in communication with the pore pressure port 180 via a line 186. Wiring 134 extends from the pore pressure transducer through a channel 190 in the base 120 and exits through a hole 126 for interfacing with a monitor system for indicating and recording changes in the pressure of the pore pressure fluid.

It is preferred that the microaccumulator 184 be of the design disclosed in the co-pending application entitled "Microaccumulator For Measurement Of Fluid Volume Changes Under Pressure" filed on even date herewith and a copy of which is submitted herewith and incorporated fully herein for all purposes. Wiring 192 extends from the microaccumulator 184 for interface with a monitoring system, e.g. a computer, which may also control the microaccumulator and record the details of its operation.

In one method according to the present invention a well preserved and undisturbed rock sample cored from a wellbore is mounted with end caps according to this invention. Then, a constant isostatic confining pressure, p is applied on the rock sample in a triaxial cell. The sample's pore pressure is allowed to equilibrate with the cell's confining pressure. Pore pressure, u, is measured by a pore pressure sensor (e.g. pore pressure transducer 22, FIG. 2) in the pore pressure port and the mean effective (confining) stress, p', is defined as (p-u). The test is performed in multi-stages of axial loading and decreasing sample water content. A shear stress (increased axial load) is applied to the rock sample at the end of each test stage of a compression test. The shear test is stopped before shear failure occurs. Usually, shear failure occurs after a sample experiences about 2% axial strain for hard rocks and about 5% for very soft rocks. After the shear test, the sample is recompressed by withdrawing a small amount of water from the sample. In each stage of the test, a small amount of water is withdrawn from the sample by turning the high pressure generator (e.g. item 20, FIG. 2) outward or by adjusting the microaccumulator 184 (FIG. 4) as desired. This decreases the sample's water content by steps, thereby increasing its mean effective stress by steps since lowering the sample's water content lowers its pore pressure. When one stage is completed and the water content has been reduced, time is again allowed for the sample's pore pressure to equilibrate with the confining pressure of the confining fluid within the test cell. Once a substantially constant sample pore pressure is achieved, the next step of the loading is commenced. By calculating the sample water content and mean effective stress for each stage of the test, their relationships can be accurately defined in one multi-stage test. A drawback of using this technique for strength behavior characterization is that the shear test never reaches the peak shear strength of the rock to allow significant amount of plastic deformation. And thus the strength characteristic defined by this method may represent the lower bound strength. However, for practical use for a conservative wellbore model design, the lower bound information is sufficiently accurate for engineering design, since for most wellbore stability model designs the objective is to keep the wellbore stresses within the elastic range or at least the low plastic regime.

Figure 5:
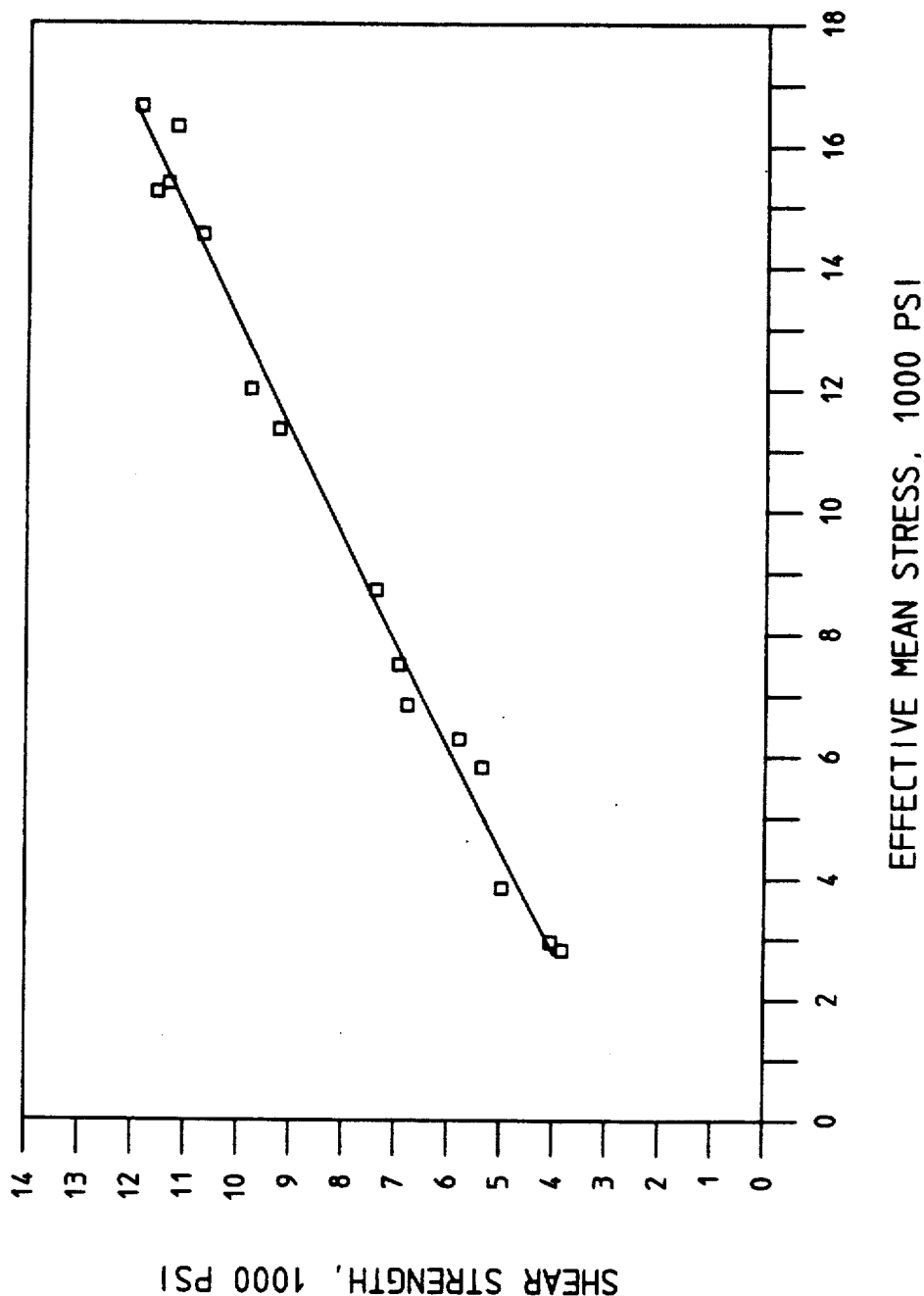
FIG. 5 presents a graph of shale strength versus mean effective stress.

FIG. 5 presents a graph of shale strength versus mean effective stress. This data was developed using the apparatuses and methods described in the copending application entitled "Methods And Apparatuses For Measurement Of The Strengths, Pore Pressures, And Mechanical Properties of Low Permeability Geologic Materials," but without changing sample water content during testing. Several tests were done on uniform cores with different water contents. However, with apparatus and methods according to this invention, only one multi-stage test is needed.

Figure 8:
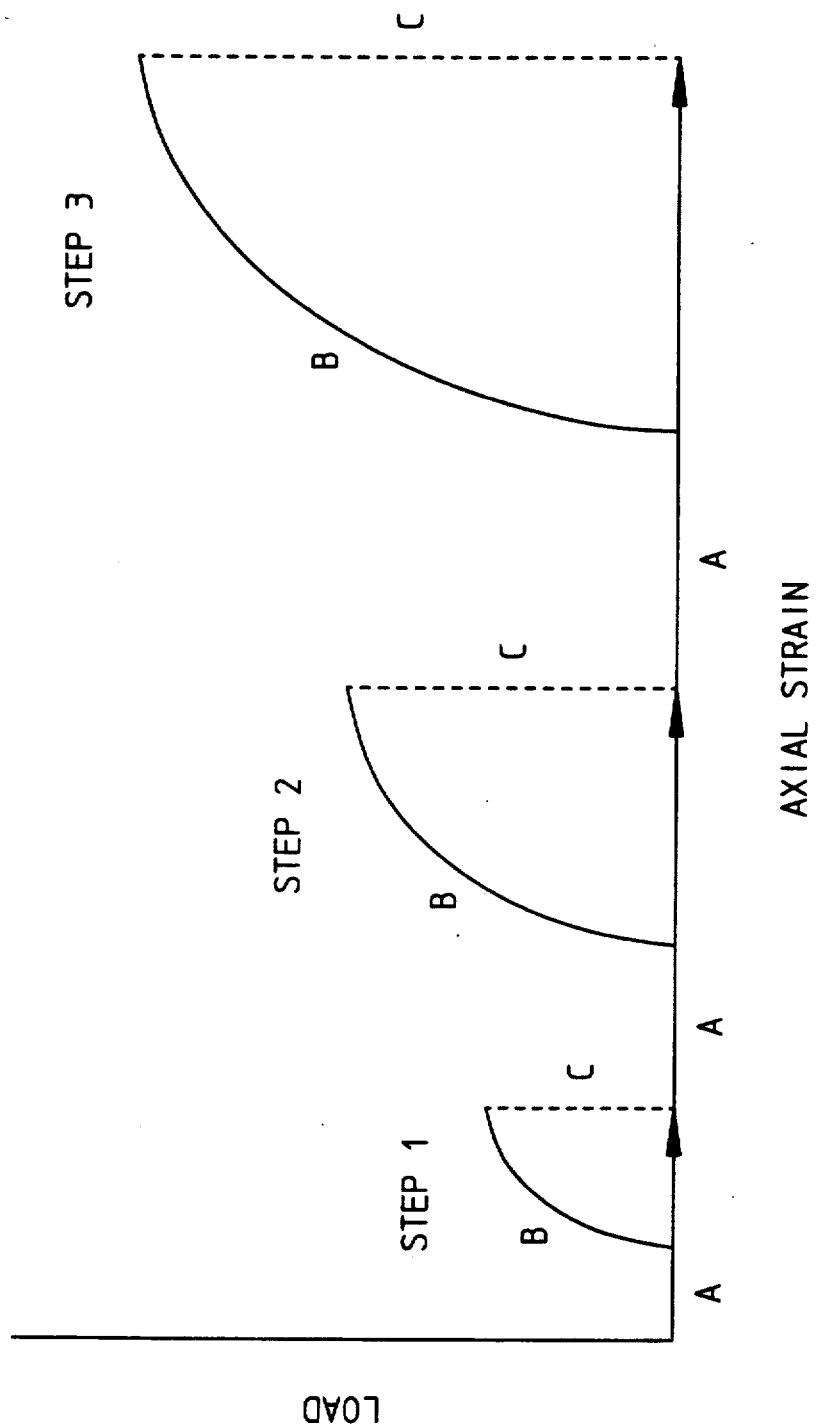
FIG. 8 is a schematic presentation of a test according to the present invention.

FIG. 8 presents schematically a test according to the present invention. It depicts three steps (1, 2, and 3) each including sub-steps A, B, and C. The vertical axis in FIG. 8 is "Load," i.e., the compressive load of a load piston on a rock sample in a triaxial test cell. The horizontal axis is "Strain."

In Step A, a constant isostatic confining pressure of a confining fluid at a desired level is applied to the sample. The sample's pore pressure is allowed to equilibrate with the pressure of the confining fluid and water is allowed to drain from the sample by adjusting the pressure generator or microaccumulator so that pore pressure is less than confining pressure.

In Step B the sample is gradually loaded by the load piston until it almost reaches a failure condition. This is noted by observing a screen (e.g. a computer monitor screen interfaced with the indicators on the sample) which shows a curve of axial load versus axial strain.

In Step C, the load on the sample is released. Then the confining pressure is increased and the sample is again allowed to equilibrate with the confining pressure, thus reaching a new sample pore pressure and new mean effective stress.

During this step-wise test, a plurality of steps (more than one) each including sub-steps A, B, C are conducted on one sample. The test produces a strength (or failure) envelope for that rock.

Figure 9:
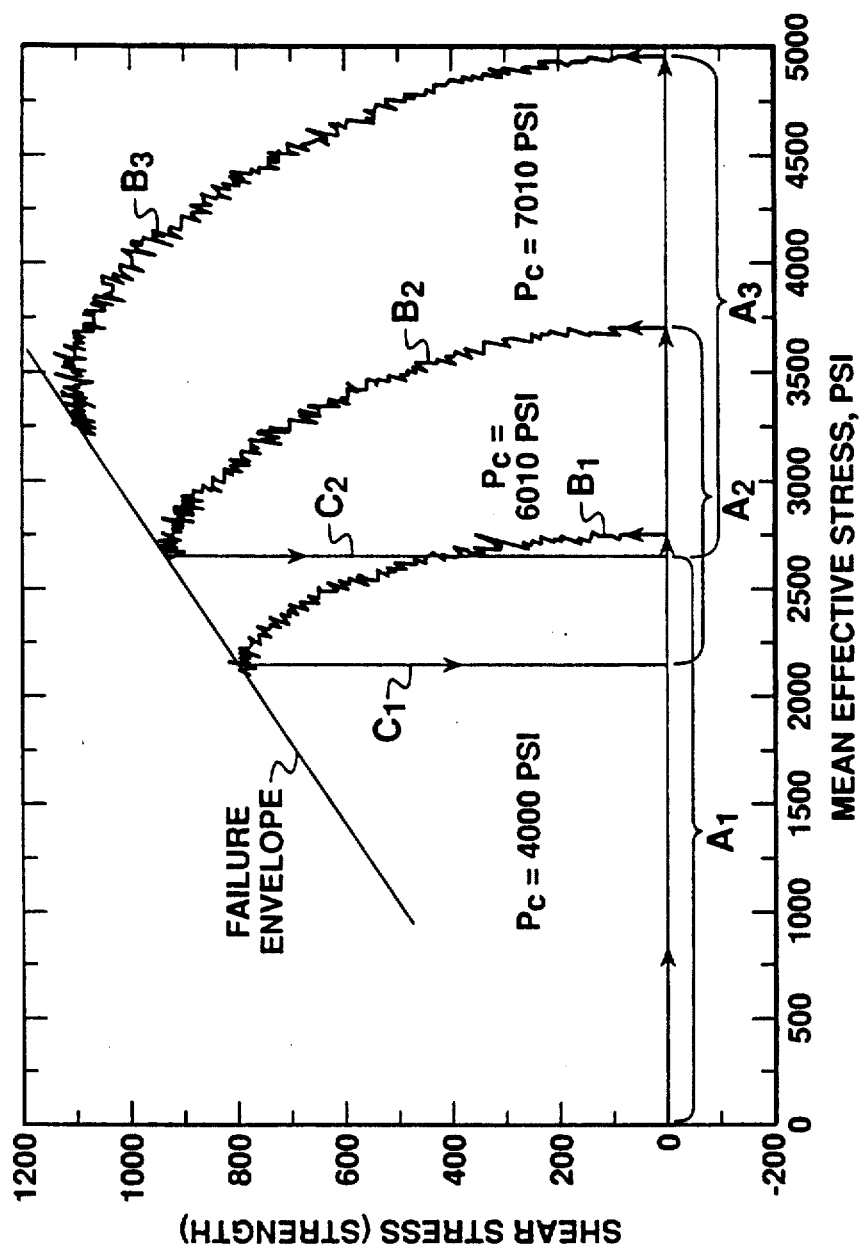
FIG. 9 presents data from a test according to the present invention.

FIG. 9 presents data for a three stage step-wise test of a shale according to the present invention. The vertical axis in FIG. 9 presents the load on the sample in p.s.i. The horizontal axis presents the mean effective stress in p.s.i. (which here is the same as the sample's mean effective stress at zero load).

The parameters for each stage of the test are:

| STAGE 1 | |
|---|---|
| Confining Pressure ($A_1$) | 4000 p.s.i. |
| Pore Pressure (at equilibrium with confining pressure) | 1269 p.s.i. |
| Load of Piston on sample ($B_1$) | 1724 p.s.i. |
| Strength | 810 p.s.i. |
| Axial Strain at this Load | 45.61 milli strains |
| Pore Pressure near shear failure | 2426 p.s.i. |
| Load after piston released | 0 |
| Pore Pressure after piston released | 2004 p.s.i |

In this stage, the sample was loaded to a shear load of 1724 p.s.i.; then water was allowed to drain from the sample as the load was reduced to zero and confining pressure increased to 6010 p.s.i., at which point the pore pressure was 2004 p.s.i.

| STAGE 2 | |
|---|---|
| Confining Pressure ($A_2$) | 6010 p.s.i. |
| Pore Pressure (at equilibrium with confining pressure) | 2350 p.s.i. |
| Load of Piston on Sample ($B_2$) | 1992 p.s.i. |
| Strength | 938 p.s.i. |
| Axial Strain at this Load | 88.40 milli strains |
| Pore Pressure near shear failure | 4030 p.s.i |

| -continued | |
|---|---|
| STAGE 2 | |
| Load after piston released | 0 |
| Pore Pressure after piston released | 2008 p.s.i. |

In this stage, the confining pressure was increased to 6010 p.s.i. at which point its equilibrium pore pressure was 2350 p.s.i. Then the sample was loaded at 1992 p.s.i. resulting in an axial strain of 88.40 strains at which point the pore pressure was 4030 p.s.i. Again the load was decreased to zero at which point the pore pressure was 2008 p.s.i. Then stage 3 was started by letting water drain from the sample as the load was reduced to zero and the confining pressure was increased to 7010 p.s.i.

| STAGE 3 | |
|---|---|
| Confining Pressure ($A_3$) | 7010 p.s.i. |
| Pore Pressure (at equilibrium with confining pressure) | 2045 p.s.i. |
| Load of Piston on Sample ($B_3$) | 2413 p.s.i. |
| Strength | 1136 p.s.i. |
| Axial Strain at this Load | 144.50 milli strains |
| Pore Pressure near shear failure | 4261 p.s.i. |
| Load after Piston released | 0 |
| Pore Pressure after Piston released | 0 |

Thus a "failure envelope" is developed by drawing a curve through the Points approaching peak stress (strength). This envelope shows strength is a function of mean effective stress.

Figure 6:
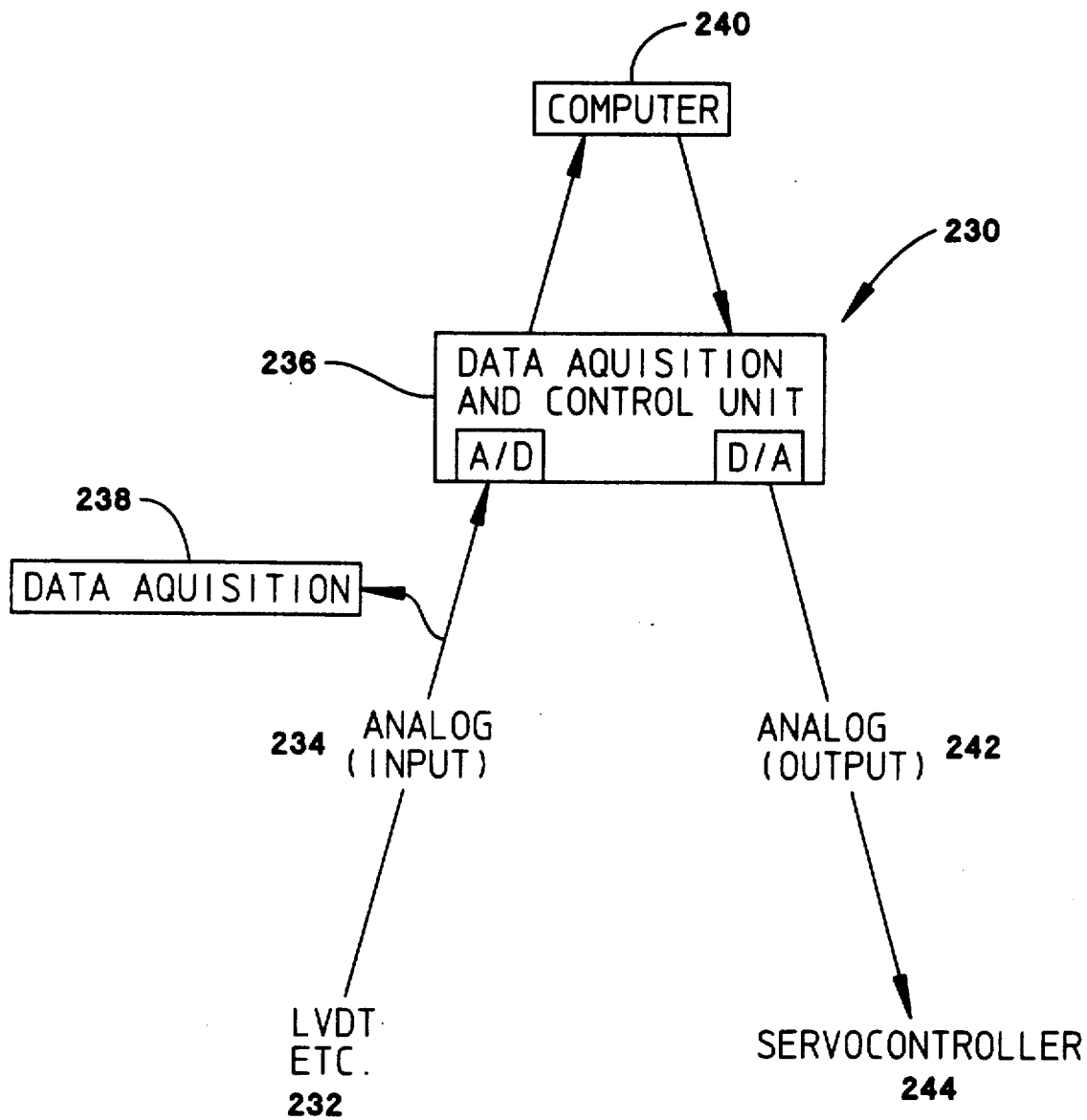
FIG. 6 presents in schematic form a data acquisition system used with the present invention.

Referring now to FIG. 6, a data acquisition and control system 230 is shown which is utilized with an apparatus such as the apparatus of FIGS. 2, 3 and 4 to monitor and control the rate of axial loading of a test specimen and the expulsion of additional sample fluid from the sample and to monitor and record data. An LVDT 232 (or LVDT's; e.g. as the LVDT's in FIG. 4) (or other measuring device such as a pore pressure transducer; confining pressure transducer; or radial strain transducer) provides analog signal input 234 to a data acquisition and control unit 236; e.g. a signal representative of axial strain within a certain time period. Input is also provided to data acquisition 238 for recording axial strain versus axial load. The data from unit 236, in digital form is provided to a computer 240 which compares the axial strain rate or strain within a certain time period to a chosen strain rate and sends a signal in digital form to the unit 236 which, in turn, provides an analog output signal 242 to operate servocontroller (or controllers) 244 which control valves to affect axial load.

Figure 7:
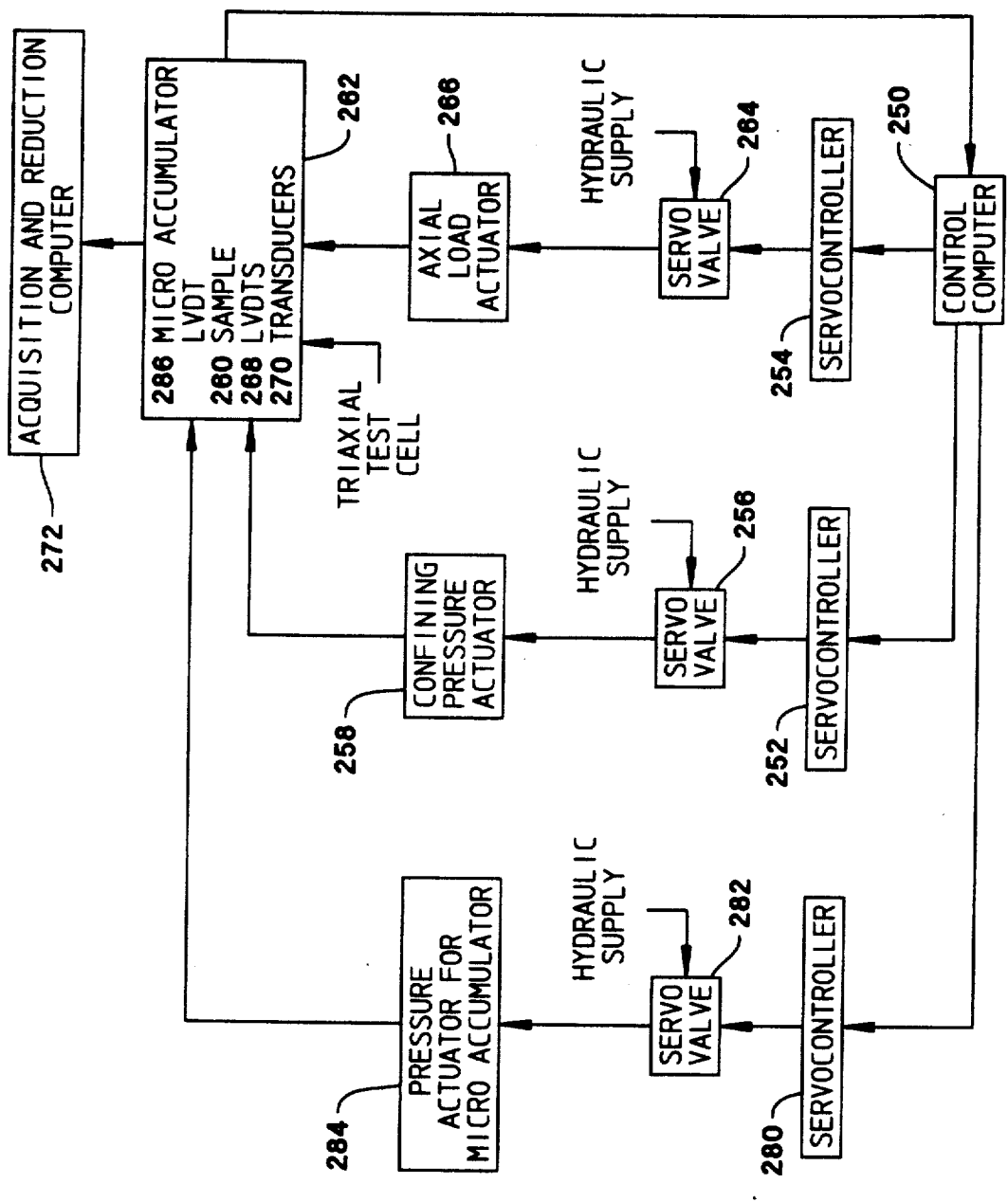
FIG. 7 presents schematically a computer control system used with the present invention.

As illustrated in FIG. 7, a control computer 250 (like the computer 240 of FIG. 5; e.g. an IBM AT PC computer) provides an analog output signal to servocontrollers 252, 254 and 280. The servocontroller 252 controls a servovalve 256 which affects the supply of hydraulic fluid to a confining pressure actuator 258. The actuator 258 provides th pressurized hydraulic fluid about a test sample 260 in a triaxial test cell 262 like the apparatus of FIG. 2.

The servocontroller 254 controls a servovalve 264 which affects the supply of hydraulic fluid to an axial load actuator 266. The actuator 266 provides pressurized fluid to a piston which imparts an axial load to an end cap, such as the end cap 212 of the apparatus 210. The sample 260 may have various LVDT's 268 associated therewith, as well as transducers 270, which sense changes in the sample 260 and provide data to an acquisition and reduction computer 272 (like computer 20 in FIG. 2). The servocontroller 280 controls a servovalve 282 which affects the supply of hydraulic fluid to an accumulator actuator 284. The actuator 284 provides pressurized fluid to the accumulator piston which imports a pressure on the pore pressure fluid. The accumulator LVDT 286 senses changes in the sample pore volume and provides data to an acquisition and reduction computer 272.

Figure 10:
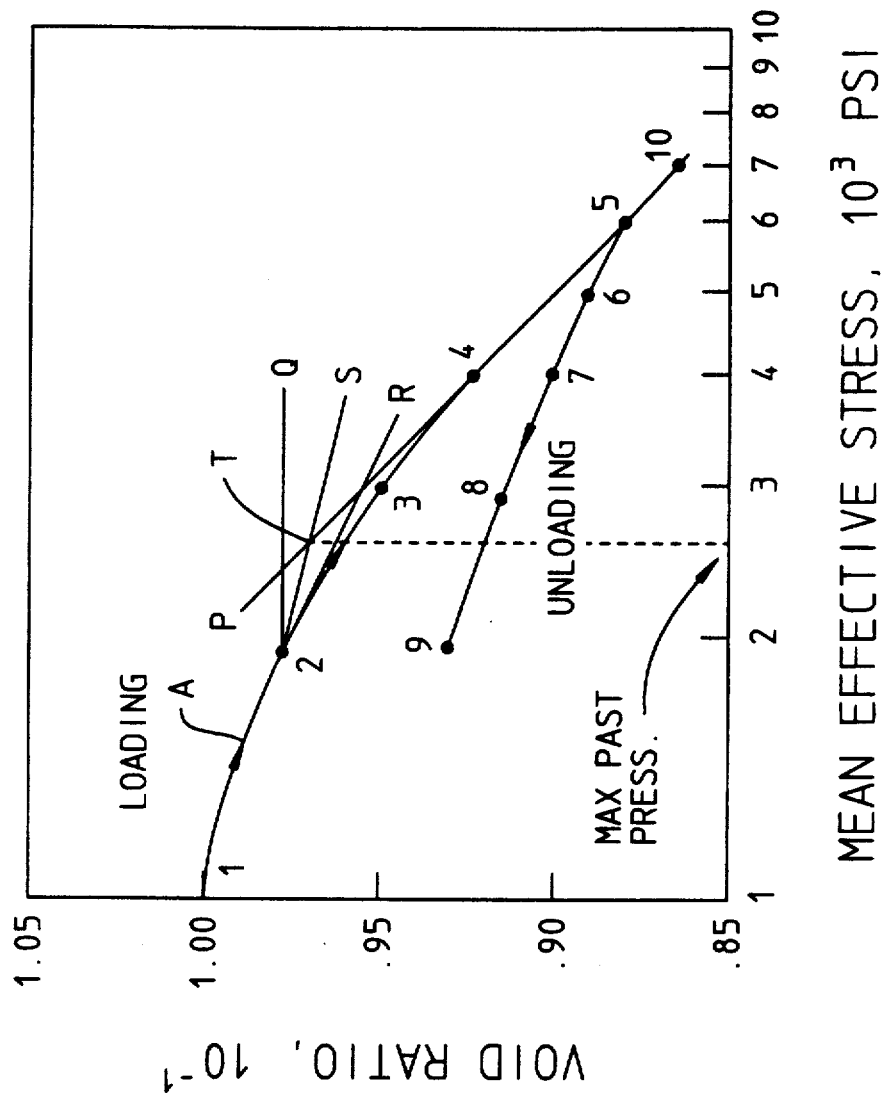
FIG. 10 presents test data from tests according to the present invention.

As shown in FIG. 10, it is possible according to the present invention to determine the maximum past overburden pressure to which a geologic material has been subjected. A sample is progressively loaded, increasing confining pressure, (curve A) and then unloaded, decreasing confining pressure (curve B) while maintaining pore pressure constant (in this case 2000 p.s.i. The confining pressure at each point is as follows (in p.s.i.).

1. 4000
2. 5000
3. 6000
4. 7000
5. 8000
6. 7000
7. 6000
8. 5000
9. 4000
10. 9000 (confirmation point)

For each point the mean effective stress is determined and correlated with the void ratio (porosity) (determined form the amount of water expelled from the sample). Plotting these values yields curves A and B. Although methods are known in the prior art for determining preconsolidation loads, Applicants are unaware of the use of such methods for determining the maximum post pressure to which a low permeability rock has been subjects. The prior art process of graphically estimating the value of a maximum consolidation stress is present at pages 297-299 of "Soil Mechanics" edited by T. Williams Lambe et al and published by John Wiley & Sons, Inc. in 1969. For the situation of FIG. 10, this determination is as follows:

1. Determine point of maximum curvature.
2. Draw a horizontal line PQ.
3. Draw a tangent PR at P.
4. Draw the line PS bisecting the angle QPR
5. Draw a straight line backward from the lower portion of the curve to intersect PS at T.
6. From T, draw a vertical line to the X-axis, yielding maximum past pressure (stress).

Figure 11:
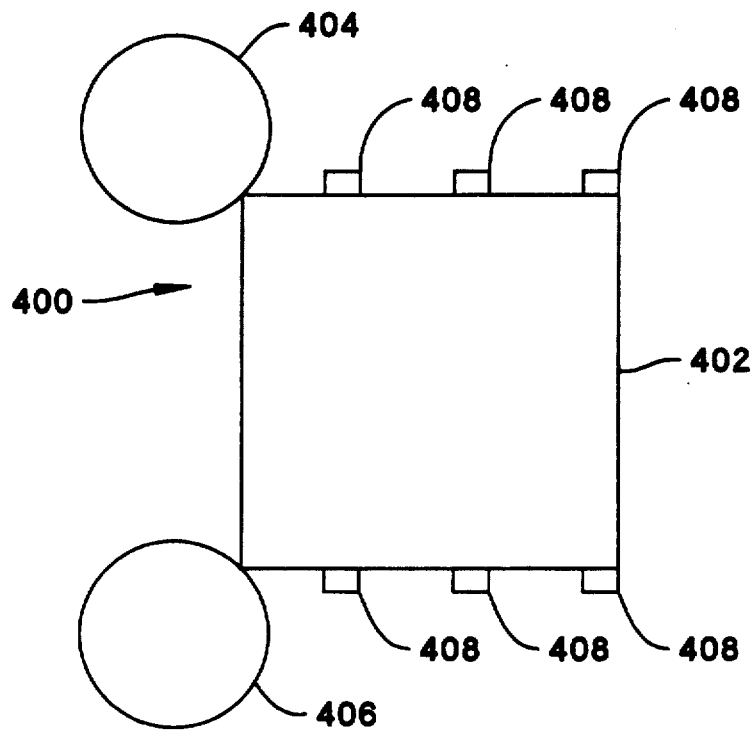
FIGS. 11, 12 and 13 show schematically screen members according to the present invention.

As shown in FIG. 11, a screen member 400 according to the present invention for enclosing a sample to facilitate the flow of sample fluid therefrom has a main square portion 402 for encircling the side wall of a cylindrical sample and two circular portions 404, 406 connected thereto for folding over the circular ends of a sample. Tabs 408 fold over the circular portions to provide further flow areas.

Figure 12:
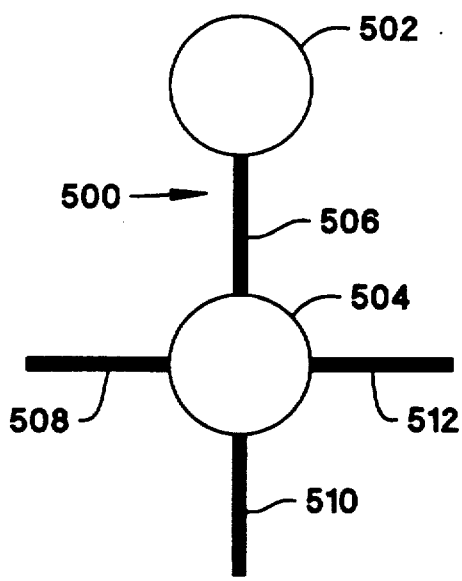

As shown in FIG. 12, the entire square portion 402 of the device in FIG. 11 is not needed to facilitate flow. A screen member 500 has two circular screen portions 502 and 504 interconnected by a thin piece of screen 506. Pieces of screen 508 and 510, and 512 extend from the circular portion 504 so that upon folding of the two circular portions onto the ends of a cylindrical sample the pieces 508, 510 and 512 are folded to contact the circular portion 502. Tabs may be used at the ends of the pieces 508, 510 and 512.

Figure 13:
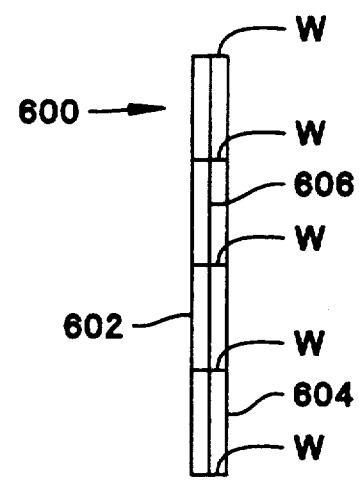

Any of the screens or pieces of screens in devices such as the screen members previously described can be formed from multi-component screens. For example, as shown in FIG. 13, a screen 600 having three screen components 602, 604, and 606 spot welded together at points W. The screens may be of different mesh. In the particular embodiment FIG. 13, the screen 602 is 300 mesh and the screen 604 is 300 mesh. These relatively fine screens prevent the sample or the flexible jacket from entering the screen 606 which is of a coarser mesh, e.g. 100 mesh, thereby insuring that the screen 606 is not blocked and serves as a good flow path.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

We claim:

1. A step-wise test method for triaxially testing a single sample of a material at different pore pressures in a single test procedure to obtain strength values for the sample, the sample having two ends and prepared and mounted by mounting a pore pressure transducer in a pore pressure chamber in a first end cap of a triaxial test apparatus, the pore pressure chamber in fluid communication with a pore pressure channel extending to a surface of the first end cap for disposition contactingly adjacent the rock sample to be tested, the pore pressure channel for receiving sample fluid expelled from the sample during testing, the pore pressure channel and the pore pressure chamber filled with an inert fluid immiscible with the sample fluid, and a flexible impermeable jacket applied to the sample other than to the sample's ends, and applying the first end cap to one end of the sample and a second end cap to the other end of the sample, the sample having a pore pressure, the pore pressure chamber in fluid communication via a flow line having a valve thereon for controlling flow with a pressure generator having a cavity for receiving an amount of the inert immiscible fluid from the pore pressure chamber, the test method comprising placing the sample in a confinement vessel of a triaxial test apparatus and sealing the vessel shut, isostatically loading the sample by introducing a confining fluid under pressure into the confinement vessel to provide a constant confining pressure on the sample to consolidate the sample and allow it to reach a predetermined pore pressure, interconnecting the pore pressure transducer with a monitor system outside of the test apparatus, and then opening the valve, allowing the sample to consolidate and sample fluid to flow from the sample into the pore pressure channel by adjusting the pressure generator so that the cavity receives an amount of inert immiscible fluid corresponding to the amount of sample fluid flowing from the sample until the sample's pore pressure equilibrates with pressure in the pore pressure chamber, and then closing the valve, applying a load piston to one end cap to apply a load on the sample which approaches the shear failure level of the sample, the piston sealingly extending through the confinement vessel to contact the sample, measuring and recording pore pressure of the sample and load thereon continuously during loading of the sample, releasing load on the sample, changing the confining pressure to a new confining pressure on the sample and opening the valve to allow sample fluid to flow into or out of the pore pressure channel with a corresponding flow of inert immiscible fluid into or out of the pressure generator's cavity, permitting the sample's pore pressure to equilibrate with the new confining pressure until fluid stops flowing from or into the sample, and then closing the valve, at a new pore pressure, and measuring and recording a new pore pressure of the sample and load thereon following application a load by the piston which again approaches the shear failure level of the sample.

2. The method of claim 1 wherein the sample is rock.

3. The method of claim 1 wherein the rock is low permeability rock.

4. The method of claim 1 including
   prior to sealing the vessel applying strain indicators to the sample,
   connecting the strain indicators to a monitor/control system and
   measuring and recording axial and radial strain of the sample continuously during the test.

5. The method of claim 4 including loading the sample past a peak shear strength of the sample to a residual stress level and beyond and recording data resulting from such loading.

6. The method of claim 4 including, prior to filling the pore pressure channel and the pore pressure chamber with the inert immiscible fluid,
   evacuating substantially all air from the pore pressure channel and from the pore pressure chamber.

7. The method of claim 1 including obtaining a new pore pressure by repeating the steps of claim 1 to obtain a plurality of additional pore pressure readings.

8. The method of claim 1 wherein the pressure generator has a piston movably and adjustably disposed in the cavity so that by adjustably moving the piston the volume of the cavity is adjusted.

* * * * *